US 8,076,388 B2

(12) United States Patent
Shalaby et al.

(10) Patent No.: US 8,076,388 B2
(45) Date of Patent: Dec. 13, 2011

(54) SELF-SETTING POLYMERIC CYANOACRYLATE COMPOSITES

(75) Inventors: Shalaby W Shalaby, Anderson, SC (US); Michael Aaron Vaughn, Clemson, SC (US); Shawn J Peniston, Easley, SC (US); Sheila Nagatomi, Seneca, SC (US)

(73) Assignee: Poly-Med, Inc., Anderson, SC (US)

( * ) Notice: Subject to any disclaimer, the term of this patent is extended or adjusted under 35 U.S.C. 154(b) by 19 days.

(21) Appl. No.: 12/080,649

(22) Filed: Apr. 4, 2008

(65) Prior Publication Data
US 2008/0220045 A1     Sep. 11, 2008

Related U.S. Application Data

(63) Continuation-in-part of application No. 11/601,994, filed on Nov. 20, 2006.

(60) Provisional application No. 60/739,996, filed on Nov. 28, 2005.

(51) Int. Cl.
*A61K 6/083* (2006.01)
*A61K 33/42* (2006.01)
*C08K 3/32* (2006.01)
*C08K 3/34* (2006.01)

(52) U.S. Cl. ........ 523/115; 523/116; 524/414; 424/444; 424/602

(58) Field of Classification Search .................. 523/115, 523/116; 424/602, 444; 524/414
See application file for complete search history.

(56) References Cited

U.S. PATENT DOCUMENTS

| | | | |
|---|---|---|---|
| 3,896,077 A * | 7/1975 | Leonard et al. | 523/177 |
| 4,192,021 A * | 3/1980 | Deibig et al. | 623/23.61 |
| 5,350,798 A | 9/1994 | Linden et al. | |
| 5,508,352 A | 4/1996 | Sasaki et al. | |
| 5,874,509 A | 2/1999 | Shalaby et al. | |
| 6,379,453 B1 | 4/2002 | Lin et al. | |
| 6,699,940 B2 | 3/2004 | Shalaby | |
| 6,723,114 B2 | 4/2004 | Shalaby | |
| 2002/0173770 A1 * | 11/2002 | Flory et al. | 604/537 |
| 2003/0032735 A1 * | 2/2003 | Kotzev | 525/412 |

* cited by examiner

*Primary Examiner* — Tae H Yoon
(74) *Attorney, Agent, or Firm* — McCormick, Paulding & Huber LLP

(57) ABSTRACT

Self-setting, absorbable bioactive polycyanoacrylate-based composites include at least one inorganic phosphate salt or a combination of at least one inorganic phosphate salt and calcium silicate in a cyanoacrylate matrix. The composites can be reinforced with single- or multicomponent absorbable, warp-knitted mesh, thus producing a broad range of absorbable, bioactive biomaterials suitable for use not only as preferred absorbable alternatives to the commercial non-absorbable polymethyl methacrylate bone cements, but also for repairing or replacing cranial and maxillofacial bone defects and other complex defects through guided bone regeneration.

12 Claims, No Drawings

SELF-SETTING POLYMERIC CYANOACRYLATE COMPOSITES

This application is a continuation-in-part of U.S. patent application Ser. No. 11/601,994, filed on Nov. 20, 2006, and entitled "Self-setting Polymeric Cyanoacrylate Composites and Applications Thereof," which claims the benefit of prior provisional application Ser. No. 60/739,996, filed Nov. 28, 2005.

FIELD OF THE INVENTION

The present invention is directed to self-setting, absorbable bioactive polycyanoacrylate-based composites comprising at least one inorganic phosphate filler with and without calcium silicate and which can be further reinforced with warp-knitted meshes to allow their applications not only as an absorbable preferred alternative to the non-absorbable polymethyl methacrylate bone cements, but also for repairing or replacing cranial and maxillofacial bone defects and other complex defects through guided bone regeneration.

BACKGROUND OF THE INVENTION

The parent application was the first to describe absorbable composites that have the integrated attributes of the (1) absorbable cyanoacrylate tissue adhesives, (2) high modulus phosphate-based microparticles as fillers in a thermoplastic matrix, and (3) absorbable phosphate glasses and their use as soluble or partially soluble calcium phosphate-based microparticles, capable of the controlled release of bioactive ions needed for bone mineralization, namely, $(PO_4)^{-3}$ and $Ca^{+2}$. The perceived clinical significance of these integrated attributes provided an incentive to pursue the studies associated with the present invention which deals with a new type of self-setting absorbable, bioactive, polymeric, cyanoacrylate composite based on flowable precursors comprising water-soluble or partially water-soluble calcium-phosphate solid microparticulates in a liquid cyanoacrylate-based matrix. In retrospect, the parent application dealt in general with self-setting, bioactive, absorbable, polymeric cyanoacrylate composites, comprising at least 20 percent by weight of inorganic phosphate microparticulate fillers, wherein the composites are capable of the controlled release of bone mineralizing ions, antimicrobials, and bone growth promoters. Such composites are useful as bone cements, fillers, and/or substitutes. More specifically, the parent application was directed to absorbable, self-setting, bioactive composite having at least 20 percent by weight of inorganic phosphate microparticles in a polymeric cyanoacrylate matrix. Preferably, the cyanoacrylate is a methoxyalkyl cyanoacrylate, most preferably methoxypropyl cyanoacrylate. In another preferred embodiment the cyanoacrylate is a mixture of an alkyl cyanoacrylate and an alkoxyalkyl cyanoacrylate. For such embodiment it is preferred that the alkyl cyanoacrylate is ethyl cyanoacrylate and the alkoxyalkyl cyanoacrylate is methoxypropyl cyanoacrylate. However, the parent application did not address the use of absorbable fabric constructs as reinforcements in the self-setting polymeric cyanoacrylate composites, which further extend their utility to orthopedic, cranial, and maxillofacial applications beyond being alternative substitutes for the traditional polymethyl methacrylate bone cement. The present invention is directed, in part, to the use of knitted, absorbable fabric for producing fiber-reinforced, mesh-setting cyanoacrylate composites. Furthermore, it has been recently reported that β-calcium silicate (β-CaSiO₃) ceramics induce a fast apatite formation and a high growth rate of apatite layer in simulated body fluid [Y. Iimori et al., *J. Mater. Sci., Mater. Med.*, 15, 1247 (2004); P. Siriphannon et al., *J. Mater. Res.*, 14, 529 (1999); P. Siriphannon et al., *J. Biomed. Mater. Res.*, 52, 30 (2000)]. It has been also reported that in vivo experiments showed that calcium silicate coating had good osteo-conduction [W. C. Xue, *Biomaterials*, 26, 3455 (2005)]. This prompted the use of calcium silicate as art of the compositions, subject of this invention, to improve the osteo-conductivity of the self-setting polymeric cyanoacrylate composites.

SUMMARY OF THE INVENTION

A major aspect of the present invention is directed to an absorbable, self-setting, bioactive composite formed of at least 20 percent by weight of solid microparticles in a polymeric cyanoacrylate matrix, the solid microparticles comprising at least one type of inorganic phosphate microparticles, the cyanoacrylate matrix derived from a liquid cyanoacrylate comprising at least one alkoxyalkyl cyanoacrylate and a reinforcing absorbable, warp-knitted mesh, wherein the liquid cyanoacrylate comprises methoxypropyl cyanoacrylate. Alternatively, the liquid cyanoacrylate comprises a mixture of methoxyalkyl and ethyl cyanoacrylates. Meanwhile, at least one type of inorganic phosphate microparticles comprises at least one member of the group consisting of anhydrous dibasic calcium phosphate ($CaHPO_4$), tricalcium phosphate [$\beta$-$Ca_3(PO_4)_2$], dibasic potassium phosphate ($K_2HPO_4$), dibasic sodium phosphate and a phosphate glass derived from CaO, $P_2O_5$, and at least one oxide selected from the group consisting of $K_2O$, $Na_2O$, MgO, ZnO, $Fe_2O_3$, and $SiO_2$. Furthermore, the absorbable, self-setting, bioactive composite can contain less than 10 percent by weight of hydroxy-terminated polyglycolide microparticles (PG-H).

A specific aspect of this invention deals with an absorbable, self-setting, bioactive composite formed at least 20 percent by weight of solid microparticles in a polymeric cyanoacrylate matrix, the solid microparticles comprising at least one type of inorganic phosphate microparticles, the cyanoacrylate matrix derived from a liquid cyanoacrylate comprising at least one alkoxyalkyl cyanoacrylate and a reinforcing absorbable, warp-knitted mesh, wherein the liquid cyanoacrylate comprises methoxypropyl cyanoacrylate, and wherein said composite comprises at least 30 percent by weight of $CaHPO_4$ microparticles and less than 10 percent by weight of hydroxy-terminated polyglycolide (PG-H) microparticles, and further wherein the warp-knitted mesh comprises a multifilament yarn made of an 88/12 mixture of l-lactide/trimethylene carbonate segmented copolymer. Additionally, the mesh can contain a second multifilament yarn made from a polyaxial, segmented copolymer of glycolide, trimethylene carbonate, and ε-caprolactone.

Another specific aspect of this invention deals with an absorbable, self-setting, bioactive composite formed of at least 20 percent by weight of solid microparticles in a polymeric cyanoacrylate matrix, the solid microparticles comprising at least one type of inorganic phosphate microparticles, the cyanoacrylate matrix derived from a liquid cyanoacrylate comprising at least one alkoxyalkyl cyanoacrylate and a reinforcing absorbable, warp-knitted mesh, wherein the reinforcing absorbable, warp-knitted mesh is constructed from at least one yarn selected from the group consisting of those made of chitosan, silk, a high lactide-based segmented copolyester, a high glycolide-based copolymer, high glycolide-based segmented polyaxial copolymer, and segmented polyether-ester. More specifically, the warp-knitted mesh comprises at least one type of multifilament yarn of absorbable polymers made by the ring-opening polymerization of at least one cyclic monomer selected from the group consisting of glycolide, l-lactide, trimethylene carbonate, ε-caprolactone, p-dioxanone, and a morpholine-dione.

Yet another aspect of this invention is directed to an absorbable, self-setting, bioactive composite formed of at least 20 percent by weight of solid microparticles in a polymeric cyanoacrylate matrix, the solid microparticles comprising at least one type of inorganic phosphate microparticles, the cyanoacrylate matrix derived from a liquid cyanoacrylate comprising at least one alkoxyalkyl cyanoacrylate and a reinforcing absorbable, warp-knitted mesh, wherein the solid microparticles further comprise calcium silicate.

A second major aspect of this invention deals with an absorbable, self-setting, bioactive composite formed of at least 20 percent by weight of mixed solid microparticles in a polymeric cyanoacrylate matrix, the mixed solid microparticles comprising at least one type of inorganic phosphate and calcium silicate, the cyanoacrylate matrix derived from a liquid cyanoacrylate comprising an alkoxyalkyl cyanoacrylate. Preferably, the liquid cyanoacrylate comprises methoxypropyl cyanoacrylate and the mixed solid microparticles comprise basic calcium phosphate ($CaHPO_4$), calcium silicate ($CaSiO_3$), and an anionic initiator selected from the group consisting of dibasic potassium phosphate, dibasic sodium phosphate, and hydroxy-terminated polyglycolide (PG-H), and the subject composite is in the form of a partially cured paste that further comprises a reinforcing absorbable, warp-knitted mesh, constructed from at least one yarn selected from the group consisting of those made of chitosan, silk, a high lactide-based segmented copolyester, a high glycolide-based copolymer, high glycolide-based segmented polyaxial copolymer, and segmented polyether-ester, and further wherein the warp-knitted mesh comprises at least one type of multifilament yarn of absorbable polymers made by the ring-opening polymerization of at least one cyclic monomer selected from the group consisting of glycolide, l-lactide, trimethylene carbonate, ε-caprolactone, p-dioxanone, and a morpholine-dione. More specifically, the warp-knitted mesh comprises a multifilament yarn made of an 88/12 mixture of l-lactide/trimethylene carbonate segmented copolymer. And the mesh can comprise a second multifilament yarn made from a polyaxial, segmented copolymer of glycolide, trimethylene carbonate, and ε-caprolactone. From a clinical perspective, all components of the composites described are sterilized and can be used as bone cements and fillers or used for repairing or substituting cranial and maxillofacial bones.

A clinically important aspect of this invention deals with an absorbable, self-setting, bioactive composite formed of at least 20 percent by weight of solid microparticles in a polymeric cyanoacrylate matrix, the solid microparticles comprising at least one type of inorganic phosphate microparticles, the cyanoacrylate matrix derived from a liquid cyanoacrylate comprising at least one alkoxyalkyl cyanoacrylate and a reinforcing absorbable, warp-knitted mesh, wherein the composite precursors comprise variable amounts of an anionic polymerization initiator and inhibitor to modulate the curing rate of the liquid cyanoacrylate, and wherein the anionic polymerization initiator is selected from the group consisting of $K_2HPO_4$, $Na_2HPO_4$, and hydroxy-terminated polyglycolide and wherein the anionic polymerization inhibitor is selected from the group consisting of $KH_2PO_4$, acid-terminated polyglycolic acid, $NaH_2PO_4$, and pyrophosphoric acid.

Another clinically important aspect of the invention deals with an absorbable, self-setting, bioactive composite formed of at least 20 percent by weight of mixed solid microparticles in a polymeric cyanoacrylate matrix, the mixed solid microparticles comprising at least one type of inorganic phosphate and calcium silicate, the cyanoacrylate matrix derived from a liquid cyanoacrylate comprising an alkoxyalkyl cyanoacrylate, wherein the composite precursors comprise variable amounts of an anionic polymerization initiator and inhibitor to modulate the curing rate of the liquid cyanoacrylate, and wherein the anionic polymerization initiator is selected from the group consisting of $K_2HPO_4$, $Na_2HPO_4$, ad hydroxy-terminated polyglycolide and wherein the anionic polymerization inhibitor is selected from the group consisting of $KH_2PO_4$, acid-terminated polyglycolic acid, $NaH_2PO_4$, and pyrophosphoric acid.

A key aspect of this invention deals with an absorbable, self-setting, bioactive composite formed of at least 20 percent by weight of solid microparticles in a polymeric cyanoacrylate matrix, the solid microparticles comprising at least one type of inorganic phosphate microparticles, the cyanoacrylate matrix derived from a liquid cyanoacrylate comprising at least one alkoxyalkyl cyanoacrylate and a reinforcing absorbable, warp-knitted mesh, wherein said composite comprises immobilized bioactive agents ionically conjugated to carboxyl-bearing microparticles and comprising at least one basic bioactive agent selected from osteogenic agents and antimicrobial agents.

Another key aspect of this invention deals with an absorbable, self-setting, bioactive composite formed of at least 20 percent by weight of mixed solid microparticles in a polymeric cyanoacrylate matrix, the mixed solid microparticles comprising at least one type of inorganic phosphate and calcium silicate, the cyanoacrylate matrix derived from a liquid cyanoacrylate comprising an alkoxyalkyl cyanoacrylate, wherein said composite comprises immobilized bioactive agents ionically conjugated to carboxyl-bearing microparticles and comprising at least one basic bioactive agent selected from osteogenic agents and antimicrobial agents.

A pharmacologically important aspect of this invention deals with an absorbable, self-setting, bioactive composite formed of at least 20 percent by weight of mixed solid microparticles in a polymeric cyanoacrylate matrix, the mixed solid microparticles comprising at least one type of inorganic phosphate and calcium silicate, the cyanoacrylate matrix derived from a liquid cyanoacrylate comprising an alkoxyalkyl cyanoacrylate, wherein the liquid cyanoacrylate comprises methoxypropyl cyanoacrylate and the mixed solid microparticles comprise basic calcium phosphate ($CaHPO_4$), calcium silicate ($CaSiO_3$), and an anionic initiator selected from the group consisting of dibasic potassium phosphate, dibasic sodium phosphate, and hydroxy-terminated polyglycolide (PG-H), and wherein said composite comprises immobilized bioactive agents ionically conjugated to carboxyl-bearing microparticles and comprising at least one basic bioactive agent selected from osteogenic agents and antimicrobial agents.

DETAILED DESCRIPTION OF PREFERRED EMBODIMENTS

In a report by Habibovic and coworkers [*Biomaterials*, 29, 944 (2008)], it was noted that (1) in the search for a synthetic biomaterial that is able to successfully replace autografting, the "gold-standard" in orthopedic and craniofacial surgery, a range of materials have been developed in the past four decades; (2) motives influencing the design of synthetic bone graft substitutes are often based upon mimicking one or more properties of natural bone since this is the intended tissue to be repaired or augmented; (3) various types of calcium-phosphate biomaterials, which resemble either the composition of bone mineral or its precursors have been developed, such as hydroxyapatite-, α- and β-tricalcium phosphate, octacalcium phosphate, and dicalcium phosphate in the form of ceramics, cements, and thin coatings—many relatively insoluble calcium-phosphate materials are osteoconductive and in some cases, even able to induce new bone formation in extra-skeletal sites; (4) in the case of large or dense bone graft substitutes, biodegradation is important for allowing simultaneous replacement of the material with new bone—this process prevents stress shielding and disadvantageous resorption of neighboring bone; (5) although calcium-phosphate materials can be degraded through cell-mediated processes (resorption), chemical dissolution is the main pathway of biodegradation—dissolution of calcium-phosphate materials is largely dependent on their chemical composition; and (6) for both dense and macroporous materials, the rate of resorption should ideally be the same as the rate of new bone formation in order to obtain a constantly stabilized repair and eventually a fully repaired bone defect without remnants of the synthetic material. These remarks and earlier reports dealing with absorbable bone substitutes and the distantly related absorbable cyanoacrylate tissue adhesives were analyzed prior to conceiving the novel combinations of the inorganic bone graft materials with the adhesive materials to yield the different, unexpected and unobvious properties contained in the parent application of this invention and the new systems subject of the instant invention.

While the parent application of this invention introduced the novel approach of integrating the adhesive and thermoplastic properties of absorbable polycyanoacrylates with the osteogenic and structural properties of selected inorganic phosphate-containing materials to yield unique self-setting, absorbable, composite bone cement/fillers, the present invention focuses on exploiting the main attributes of these composites to maximize their clinical applicability through carefully tailored value-added features. The latter include those noted below:

1. Combining the liquid cyanoacrylate component with bioactive, solid microparticles, or soluble bioactive polymers, such as (a) certain phosphate-based microparticles or their mixtures with $CaSiO_3$ microparticles that are known for being osteoconductive and can be further activated by immobilizing specific bioactive agents to, in part, render them osteoinductive as well, and/or impart antimicrobial activities; and (b) C-succinylated, absorbable copolyesters or polyether-esters carrying succinic acid side groups capable of ionic conjugation with basic bioactive agents, such as antimicrobials and cell growth-promoting agents.

2. Introducing specific compounds to accelerate or modulate the anionic polymerization of the cyanoacrylate monomer(s), as in the case of (a) pyrophosphoric acid to slow-down the anionic polymerization when the filler itself can cause polymerization; (b) hydroxy-terminated polyglycolide (PG-H) to initiate and accelerate the polymerization; and/or (c) a specific combination of the PG-H and pyrophosphoric acid to modulate the curing time to meet the application site requirements. This allows ease of handling and modulates the curing time to be in concert with the specific surgical site and procedure.

3. Using ionic conjugates of basic bioactive agents, ionically immobilized on or within carboxyl-bearing microparticles or cyanoacrylate-soluble C-succinylated polyether-esters—the basic agents can be selected from among those known to have (a) antimicrobial activities to prevent post-surgical infection; (b) cell growth-promoting effects to promote tissue regeneration; and/or (c) specific effects to increase the rate of ossification.

4. Adding $CaSiO_3$ to the phosphate component of self-setting cyanoacrylate-based absorbable composites to increase the rate of absorption (or dissolution) of the overall phosphate/silicate mixture and improve the composite osteogenic effect. This will accelerate the directed bone regeneration process.

5. Incorporating fibrous reinforcing components to increase the modulus and/or toughness as well as fatigue properties, such as using (a) chitosan chopped fibers and chitosan knitted mesh made of multifilament yarn; (b) chopped multifilament or monofilament yarns of absorbable, slow- and/or fast-absorbing copolyesters and polyether-esters; (c) woven or knitted meshes (both weft- and warp-knitted) monofilaments and/or one or more type of multifilament yarn made of fast- or slow-absorbing copolyesters or polyether-esters. Reinforcing the self-setting, absorbable, bioactive composite facilitates their use in correcting major defects, such as those encountered in maxillofacial and cranial bones as well as long bones where, for instance, the mesh is used as a scaffold for applying a partially cured paste of the cyanoacrylate-based composite. Furthermore, using fast-absorbing fibers or mesh will result in generating interconnected channels, as they absorb, in the bone cement/filler to render it osteoconductive. Acids generated as by-products of the degrading absorbable meshes or fibers will accelerate the absorption or dissolution of the phosphate-based and $CaSiO_3$ components of the composite; and (d) bi- or multicomponent weft- or warp-knitted meshes comprising fast- and slow-absorbing yarn will lead to two or more strength retention profiles that, in turn, allow a gradual or multistage load-transfer to the natural bone and hence, accelerate bone regeneration.

6. Using surface-activated reinforcing, fibrous constructs to immobilize bioactive agents or agents that can accelerate absorption or modulate the dissolution of the composite constituents. These include (a) partially base-hydrolyzed surfaces of the fibrous components to yield negatively charged substrates for binding basic bioactive agents and basic amino acids; (b) chitosan fiber with inherently basic surfaces for binding positively charged bioactive agents or amino acids—binding acids such as aspartic and citric acids on chitosan can assist in degrading absorbable polyester components of the composite; and (c) silk fibers with pendant functional side groups for osteoblast attachment.

7. Coating the mesh reinforcing component of the self-setting cyanoacrylate-based composites will allow the application of different absorbable coatings that, in turn, can be used (a) to modulate the absorption and strength retention of the mesh through using amine-bearing polymers or carboxyl-bearing polymers that are neutralized with lysine or arginine; (b) as controlled release vehicles for the predetermined release of bioactive agents, including those known for their antimicrobial and cell growth-promoting and osteogenic activities; and (c) as carriers for basic chemical compounds or basic components capable of initiating and accelerating the polymerization of acrylate monomer(s) at the mesh fibrous components to maximize the mesh/matrix adhesive joint and hence, the mechanical properties of the reinforced composite.

8. In vitro curing of unreinforced and fiber- or mesh-reinforced self-setting composites for use as machinable blocks. Composites describe in items 1 through 7 can be prepared as fully cured blocks suitable for machining or micromachining into solid orthopedic absorbable devices useful in (a) repairing different types of bone defects, including those of the limbs and feet where bone guided bone regeneration is sought; and (b) substituting part of the maxillofacial and cranial bones where natural bone will eventually replace the absorbable composites.

Further illustrations of the present invention are provided by the following examples:

Example 1

Preparation and In Vitro Testing of a Self-Setting Composite, SCC-P1 from 50/50 (Weight/Volume) of (95/5 $CaHPO_4$/PG-H)/Methoxypropyl Cyanoacrylate Hydroxy-terminated polyglycolide (PG-H) microparticles are dried at 110° C. for at least 6 hours under reduced pressure (the microparticulate, PG-H, was made previously at Poly-Med, Inc., Anderson, S.C.). A batch of $CaHPO_4$ microparticles is dried for at least 6 hours at 130° C. A dry 5 g mixture of 95/5 $CaHPO_4$/PG-H microparticles is added, while stirring, using a Teflon-coated stirrer, under dry nitrogen atmosphere to 5 mL of MPC at room temperature. After mixing, the resulting paste is transferred to a two-part Teflon mold designed to produce cured 3×1×0.19 cm test specimens (for the 3-point bend method). The closed mold is heated at 37° C. until full curing is achieved—the approximate curing time is predetermined during a few pilot runs. The cured composition is removed and evaluated for mechanical properties using the 3-point bend method and an MTS MiniBionix universal Tester to record the peak stress, modulus and breaking elongation. A few of the cured specimens are cut into 10×10×1.9 mm samples for determining the composite absorption under accelerated conditions in deionized water at 50° C., in terms of mass loss after 10 days of incubation. To determine the molecular weight of the polymerized MPC (PMPC) the composition is extracted with chloroform. After removing the solvent, the molecular weight of the PMPC is determined by GPC using methylene chloride as the mobile phase.

Examples 2 and 3

Preparation and In Vitro Testing of Self-Setting Composites SCC-P2 and SCC-P3

The preparation and testing for SCC-P2 and SCC-P3 are conducted as described for SCC-P1 in Example 1 with the exception of using 97/3 (by weight) $CaHOP_4$/PG-H. Key data on the composite preparation and in vitro testing are summarized in Table I.

Examples 4 and 5

Preparation and In Vitro Testing of Self-Setting Composites SCC-P4 and SCC-P5

The preparation and testing of SCC-P4 and SCC-P5 are conducted as described for SCC-P1 with the exception of using 40/60 (95/5 $CaHPO_4$/PG-H)/methoxypropyl cyanoacrylate and 40/60 (95/5 $CaHPO_4$/$K_2HPO_4$)/methoxypropyl cyanoacrylate for SCC-P4 and SCC-P5, respectively. Key data on the preparation and in vitro testing are summarized in Table I.

Example 6

Preparation and In Vitro Testing of Self-Setting Composites Based on Phosphate/Silicate Microparticles and Methoxypropyl Cyanoacrylate (MPC), SCC-PS1 to SCC-PS3

Preparation of SCC-PS1 to SCC-PS3 is conducted as described for SCC-P1 (Example 1) with the exception of substituting 10 to 30 weight percent of the $CaHPO_4$ with $CaSiO_3$. Similarly, the cured composites are tested as noted in Example 1 for SCC-P1. Key data for the composite preparation and in vitro testing are summarized in Table II.

TABLE II

Projected Experimental Data for the Preparation and In Vitro Testing of SCC-PS1 to SCC-PS3

| | Composite Preparation | | Composite Properties[a] | | | | | | |
|---|---|---|---|---|---|---|---|---|---|
| | Solid/ | Weight Ratio of Solid | Full Cure, | Mechanical Properties[c] | | | | Polymeric | % Mass Loss[d] |
| Number SCC- | MPC, g/mL | Components[b] $CaHPO_4$/$CaSiO_3$/PG-H | Time, Hr (@ 37° C.) | T, mm | P.S. Kpsi | Mod. Kpsi | B.E., % | Matrix[c], $M_w$ (Kda) | @ 50° C./ 10 Days |
| PS1 | 50/50 | 87/10/3 | <2.0 | 1.9 | 325 | 50 | 5.9 | 480 | 27 |
| PS2 | 50/50 | 77/20/3 | <1.5 | 1.9 | 315 | 49 | 5.8 | 470 | 30 |
| PS3 | 50/50 | 67/30/3 | <1.0 | 1.9 | 310 | 49 | 5.6 | 470 | 32 |

[a]Tested using 3-point bend method with 3 × 1 × 0.19 cm test specimen; T = sample thickness, P.S. = peak stress, Mod. = flexural modulus, B.E. = breaking elongation.
[b]PG-H = hydroxy-terminated polyglycolide as an inhibitor.
[c]On fiber-free polymethoxypropyl cyanoacrylate.
[d]Using 20 mL of deionized water and 10 × 10 × 1.9 mm test specimen.

TABLE III

Projected Experimental Data for the Preparation and In Vitro Testing of Mesh-reinforced Composites of SCC-P3 and SCC-PS2[a]

| Reinforced Composite Number R-SCC- | Composite Preparation[b] | | Composite Properties | | | | Polymeric Matrix[d], $M_w$ (Kda) |
|---|---|---|---|---|---|---|---|
| | Single Component Composition | Bicomponent Mesh Composition | Mechanical Properties[c] | | | | |
| | | | T, mm | P.S, Kpsi | Mod. Kpsi | B.E., % | |
| P3 | SAY | N/A | 1.9 | 320 | 54 | 6.9 | 450 |
| P3 | N/A | 80/20 SAY/FAY | 1.9 | 325 | 56 | 6.6 | 455 |
| PS2 | SAY | N/A | 1.9 | 300 | 55 | 6.7 | 475 |
| PS2 | N/A | 80/20 SAY/FAY | 1.9 | 305 | 58 | 6.5 | 470 |

[a]SCC-P3 = self-setting, methoxypropyl cyanoacrylate-based/phosphate composite from Example 3; SCC-PS2 = self setting methoxypropyl cyanoacrylate-based/phosphate/silicate from Example 6.
[b]Single-component mesh = warp-knitted mesh constructed from slow-absorbing multifilament yarn, SAY of Example 7; Bicomponent mesh = warp-knitted mesh constructed from SAY and a fast absorbing multifilament yarn, FAY of Example 8.
[c]On a 3 × 1 cm test specimen having an approximately 1.9 mm thickness, using a 3-point bend method to determine the peak stress (P.S.), Flexural modulus (Mod.) and breaking elongation (B.E.). T = approximate thickness 1.9.
[d]On filler-free polymethoxypropyl cyanoacrylate matrix using GPC.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicants hereby disclose all subranges of all ranges disclosed herein. These subranges are also useful in carrying out the present invention.

What is claimed is:

1. An absorbable, self-setting, bioactive composite paste comprising at least 20 percent by weight of mixed solid calcium silicate microparticles in a cyanoacrylate matrix, the mixed solid microparticles further comprising at least one inorganic phosphate, the cyanoacrylate matrix comprising a liquid cyanoacrylate comprising an alkoxyalkyl cyanoacrylate;
and wherein the liquid cyanoacrylate comprises methoxypropyl cyanoacrylate and the at least one inorganic phosphate comprises anhydrous basic calcium phosphate ($CaHPO_4$), and the mixed solid microparticles further comprise an anionic initiator selected from the group consisting of dibasic potassium phosphate, dibasic sodium phosphate, and hydroxy-terminated polyglycolide (PG-H).

2. An absorbable, self-setting, bioactive composite paste as in claim 1 further comprising immobilized bioactive agents ionically conjugated to carboxyl-bearing microparticles and comprising at least one basic bioactive agent selected from osteogenic agents and antimicrobial agents.

3. An absorbable, self-setting, bioactive composite comprising at least 20 percent by weight of mixed solid microparticles in polymeric cyanoacrylate matrix, the mixed solid microparticles comprising at least one inorganic phosphate and calcium silicate, and the cyanoacrylate matrix derived from a liquid cyanacrylate comprising an alkoxyalkyl cyanoacrylate, in the form of a partially cured paste that further comprises a reinforcing absorbable, wrap-knitted mesh, constructed from at least one yarn selected from the group consisting of those made of chitosan, silk, a high lactide-based segmented copolyester, a high glycolide-based copolymer, high glycolide-based segmented polyaxial copolymer, and segmented polyether-ester.

4. An absorbable, self-setting, bioactive composite paste as in claim 3 wherein the wrap-knitted mesh comprises at least one multifilament yarn of absorbable polymers made by the ring-opening polymerization of at least one cyclic monomer selected from the group consisting of glycolide, l-lactide, trimethylene carbonate, ε-caprolactone, p-dioxanone, and a morpholinedione.

5. An absorbable, self-setting, bioactive composite paste as in claim 3 wherein the wrap-knitted mesh comprises a multifilament yarn made of 88/12 mixture of l-lactide/trimethylene carbonate segmented copolymer.

6. An absorbable, self-setting, bioactive composite paste as in claim 5 further comprising a second multifilament yarn made from a polyaxial, segmented copolymer of glycolide, trimethylene carbonate, and ε-caprolactone.

7. An absorbable, self-setting, bioactive composite paste as in claim 3 in the form of sterilized components for use in repairing or substituting cranial and maxillofacial bones.

8. An absorbable, self-setting, bioactive composite paste comprising at least 20 percent by weight of mixed solid calcium silicate microparticles in a cyanoacrylate matrix, the mixed solid microparticles further comprising at least one inorganic phosphate, the cyanoacrylate matrix comprising a liquid cyanoacrylate comprising an alkoxyalkyl cyanoacrylate, wherein the paste is in the form of sterilized components for use as a bone cement and filler.

9. An absorbable, self-setting, bioactive composite paste comprising at least 20 percent by weight of mixed solid calcium silicate microparticles in a cyanoacrylate matrix, the mixed solid microparticles further comprising at least one inorganic phosphate, the cyanoacrylate matrix comprising a liquid cyanoacrylate comprising an alkoxyalkyl cyanoacrylate, and wherein the liquid cyanoacrylate comprises methoxypropyl cyanoacrylate and the at least one inorganic phosphate comprises anhydrous basic calcium phosphate ($CaHPO_4$), and the mixed solid microparticles further comprise an anionic initiator selected from the group consisting of dibasic potassium phosphate, dibasic sodium phosphate, and hydroxy-terminated polyglycolide (PG-H);
and the paste is in the form of sterilized components for use as a bone cement and filler.

10. An absorbable, self-setting, bioactive paste as in claim 8 further comprising variable amounts of an anionic polymerization initiator and inhibitor to modulate the curing rate of the liquid cyanoacrylate.

11. An absorbable, self-setting, bioactive composite paste, as in claim 10 wherein the anionic polymerization initiator is selected from the group consisting of $K_2HPO_4$, $Na_2HPO_4$, and hydroxy-terminated polyglycolide and wherein the anionic polymerization inhibitor is selected from the group consisting of $KH_2PO_4$, acid-terminated polyglycolic acid, $NaH_2PO_4$, and pyrophosphoric acid.

12. An absorbable, self-setting, bioactive composite paste as in claim 8 further comprising immobilized bioactive agents ionically conjugated to carboxyl-bearing microparticles and comprising at least one basic bioactive agent selected from osteogenic agents and antimicrobial agents.

* * * * *